(12) United States Patent
Reddy et al.

(10) Patent No.: US 8,013,150 B2
(45) Date of Patent: Sep. 6, 2011

(54) PROCESS FOR THE PREPARATION OF EZETIMIBE

(75) Inventors: Manne Satyanarayana Reddy, Hyderabad (IN); Muppa Kishore Kumar, Hyderabad (IN); Maram Reddy Sahadeva Reddy, Hyderabad (IN)

(73) Assignee: MSN Laboratories Ltd., Andhra Pradesh (IN)

( * ) Notice: Subject to any disclaimer, the term of this patent is extended or adjusted under 35 U.S.C. 154(b) by 731 days.

(21) Appl. No.: 11/922,358

(22) PCT Filed: Feb. 17, 2006

(86) PCT No.: PCT/IN2006/000053
§ 371 (c)(1),
(2), (4) Date: May 9, 2008

(87) PCT Pub. No.: WO2006/137080
PCT Pub. Date: Dec. 28, 2006

(65) Prior Publication Data
US 2009/0048441 A1    Feb. 19, 2009

(30) Foreign Application Priority Data
Jun. 22, 2005   (IN) .............................. 781/CHE/2005

(51) Int. Cl.
*C07D 205/08* (2006.01)
*C07D 263/26* (2006.01)

(52) U.S. Cl. ...................... 540/200; 548/230

(58) Field of Classification Search .................. 540/200; 548/230
See application file for complete search history.

(56) References Cited

U.S. PATENT DOCUMENTS

| | | | | |
|---|---|---|---|---|
| 3,683,006 A * | 8/1972 | Fried | ............................. | 560/118 |
| 3,787,299 A * | 1/1974 | Beck et al. | .................... | 205/418 |
| 3,948,973 A * | 4/1976 | Phillips | ........................... | 560/59 |
| 3,993,683 A * | 11/1976 | Nickl et al. | ...................... | 560/12 |
| 4,044,147 A * | 8/1977 | Nelson | ........................... | 514/533 |
| 4,076,940 A * | 2/1978 | Connor et al. | ................ | 549/415 |
| 5,767,115 A | 6/1998 | Rosenblum et al. | | |
| 5,846,991 A * | 12/1998 | Tanikawa et al. | ............ | 514/381 |
| 5,856,473 A | 1/1999 | Shankar | | |
| 2003/0013699 A1 * | 1/2003 | Davis et al. | ............... | 514/210.02 |
| 2007/0049748 A1 * | 3/2007 | Uppala et al. | .................. | 540/200 |
| 2009/0227786 A1 * | 9/2009 | Gavalda I Escude et al. | | 540/200 |

FOREIGN PATENT DOCUMENTS

| | | | |
|---|---|---|---|
| EP | 1953140 A1 * | 8/2008 | |
| WO | WO 2005/049592 A1 | 6/2005 | |
| WO | WO 2008032338 A2 * | 3/2008 | |
| WO | WO 2008096372 A2 * | 8/2008 | |

OTHER PUBLICATIONS

Rosenblum, Journal of Medicinal Chemistry, 1998, 41,973-980.*
Crimmins, J. Am. Chem. Soc. 1999, 121, 5653-5660.*
Alimardanov, Adv. Synth. Catal. 2004, 346, 1812-1817.*
Yus, European Journal of Organic Chemistry vol. 2004 Issue 18, pp. 3833-3841.*
Miller, Tetrahedron Letters vol. 39, Issue 36, Sep. 3, 1998, pp. 6441-6444.*
Manley, Organic Process Research & Development 2003, 7, 436445.*
PCT International Preliminary Examination Report, PCT/IN 2006/000053, date of report Dec. 11, 2007, 10 pp.
Castaner, R.M., et al, "Ezetimibe: Hypolipidemic, Cholesterol Absorption Inhibitor," *Drugs of the Future*, 25(7), pp. 679-685, (2000).

* cited by examiner

*Primary Examiner* — Mark Berch
(74) *Attorney, Agent, or Firm* — Hamilton, Brook, Smith & Reynolds, P.C.

(57) ABSTRACT

The present invention relates to a cost effective and industrially advantageous process for the preparation of (3R,4S)-1-(4-fluorophenyl)-3-[3(S)-3-(4-fluorophenyl)-3-hydroxypropyl)]-4-(4-hydroxyphenyl)-2-azetidinone, referred to here as Ezetimibe and represented by structural formula (I). The process comprises an multi-step reaction sequence that includes a chiral auxiliary-controlled condensation, a silyl-mediated cyclization, a palladium-catalyzed Negishi cross-coupling, and the enantioselective reduction of a ketone to a hydroxyl group.

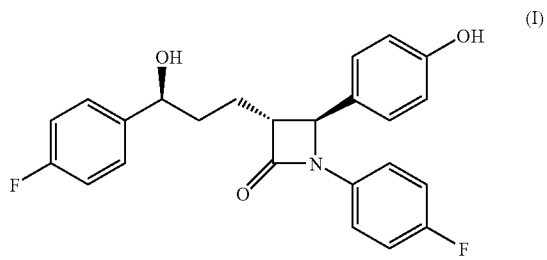

(I)

27 Claims, No Drawings

PROCESS FOR THE PREPARATION OF EZETIMIBE

RELATED APPLICATIONS

This application is the U.S. National Stage of International Application No. PCT/IN2006/000053, filed Feb. 17, 2006, published in English, and claims priority under 35 U.S.C. §365 to Indian Application No. 781/CHE/2005, filed Jun. 22, 2005.

FIELD OF THE INVENTION

The present invention relates to cost effective and industrially advantageous process for the preparation of (3R,4S)-1-(4-Fluorophenyl)-3-[3(S)-3-(4-fluorophenyl)-3-hydroxypropyl)]-4-(4-hydroxyphenyl)-2-azetidinone, referred to here as Ezetimibe. It is represented as Formula-1.

Formula-1

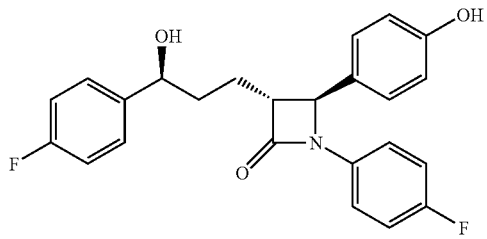

BACKGROUND OF THE INVENTION

This invention relates to an improved, cost effective and industrially advantageous process for the preparation of (3R,4S)-1-(4-Fluorophenyl)-3-[3(S)-3-(4-fluorophenyl)-3-hydroxypropyl)]-4-(4-hydroxyphenyl)-2-azetidinone (Ezetimibe), useful as cholesterol absorption inhibitor, claimed in U.S. Pat. No. 5,767,115. Preparation of Ezetimibe is also described in the above said patent. It comprises of (S)-4-phenyl-2-oxazolidinone is reacted with methyl-4-(chloroformyl)butyrate to obtain a compound of ester and it is condensed with 4-benzyloxy benzylidine (4-fluoro) aniline in the presence of titanium isopropoxide and titanium tetrachloride to give an amide compound and it is cyclised in the presence of tetrabutyl ammonium fluoride and bis trimethyl silyl acetamide to give protected lactam, it undergoes hydrolysis to give a carboxylic acid and further it reacts with p-fluoro phenyl magnesium bromide and zinc chloride in the presence of tetrakis (triphenyl phosphine) palladium to give an aromatic ketone, it is further reduced selectively in the presence of chiral catalyst to obtain an hydroxy compound and it undergoes debenzylation to give the title compound of formula-I.

By following the above process in the hydrolysis stage after completion of the reaction, pH adjusted to acidic side (below pH-4) and extracting the compound resulted more impure product because as the Lactam ring is acid sensitive, it is opened up while adjusting the pH to below 4. In the organometallic condensation reaction between acid chloride and para fluoro phenyl zinc halide, tetrakis (triphenyl phosphine) palladium is used as a catalyst which is highly expensive as well as molecular weight is higher which resulted in more byproducts and obtained compound is less pure.

The above said process is both uneconomical, inconsistency in reproducibility and more of byproduct/waste generation like triphenyl phosphine oxide, DMS, etc., and hence it is not suitable for commercial production.

Therefore, the main objective of the present invention is to prepare formula-1 through a process which is cost-effective, commercially viable, eco-friendly and consistent.

The formula-1 is prepared in the present invention, in a novel process that is cost effective and suitable for commercial scale up.

SUMMARY OF THE INVENTION

This invention provides an improved simple and cost effective, eco-friendly and well suited for commercial scale up of (3R,4S)-1-(4-Fluorophenyl)-3-[3(S)-3-(4-fluorophenyl)-3-hydroxypropyl)]-4-(4-hydroxyphenyl)-2-azetidinone, referred to here as Ezetimibe. It is represented as Formula-1.

Formula-1

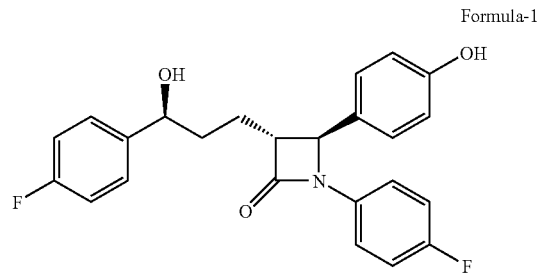

Comprising:

(a) Glutaric anhydride of formula-II reacting with an aliphatic or alicyclic alcohol in Presence of a base to give ester compound of formula-III.

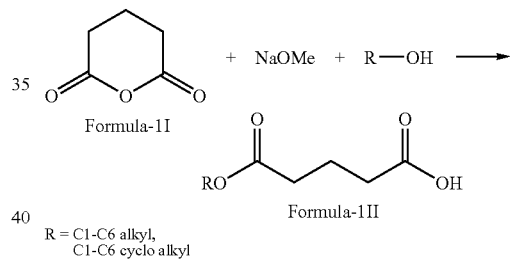

R = C1-C6 alkyl, C1-C6 cyclo alkyl (b) Using pivalyl chloride in the preparation of compound having the structural formula-V, by reacting it with compound of formula-III in presence of a acid trapping agent and subsequent reaction with chiral auxiliary of formula-IV

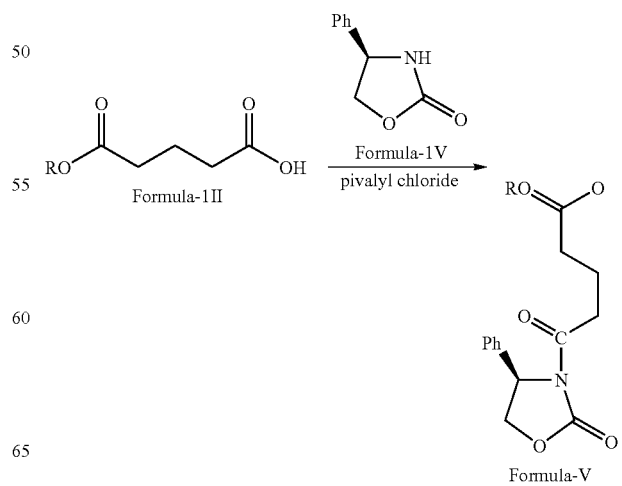

(c) Reacting the ketone of Formula-V with benzylated imine of formula-VI in presence of Lewis acid to obtain an amide of formula-VII.

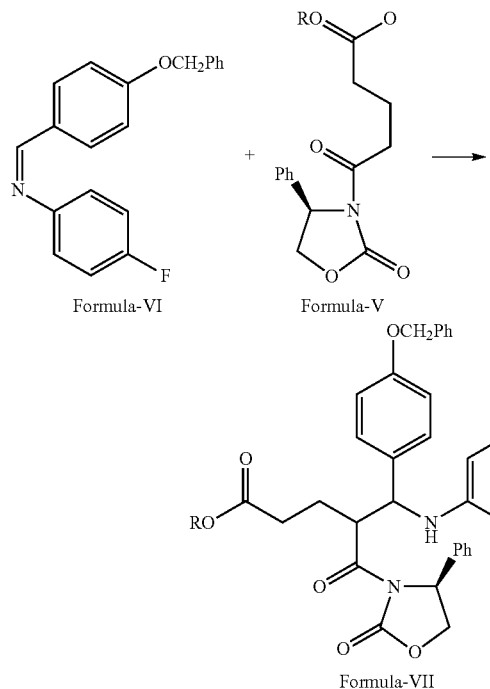

(d) Cyclizing the amide of formula VII with
  (i) a silylating agent and a fluoride ion catalyst as a cyclizating agent.
  (ii) A strong non-nucleophilic base to obtain the compound of formula-VIII.

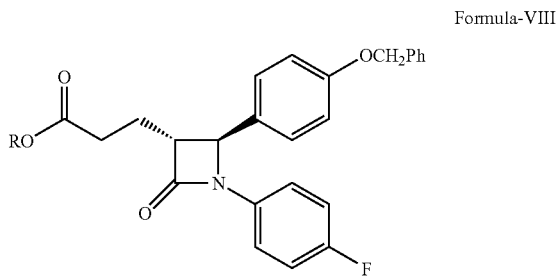

Formula-VIII (e) Hydrolising the ester group in formula VIII with a base in a suitable solvent to give the carboxylic acid compound of formula-IX. Adjusting the pH to 5-7 of hydrolysis reaction mass, preferably 6.5 to 7.0 and extraction of carboxylic acid compound of formula-IX.

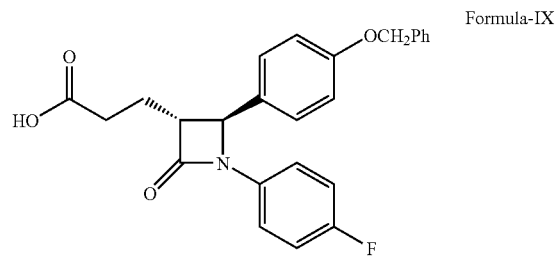

Formula-IX (f) Compound of formula-IX is converted into acid chloride and further it is converted into formula-X by organo metallic reaction in presence of a Palladium acetate as catalyst.

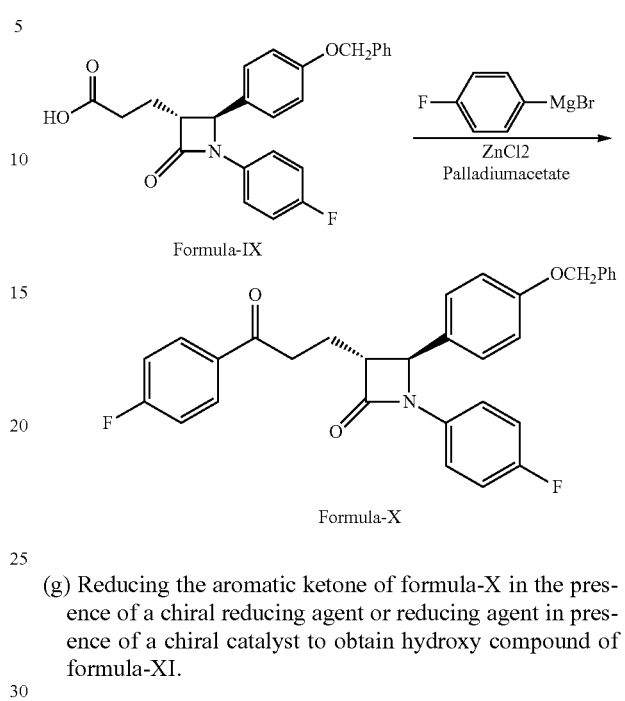

(g) Reducing the aromatic ketone of formula-X in the presence of a chiral reducing agent or reducing agent in presence of a chiral catalyst to obtain hydroxy compound of formula-XI.

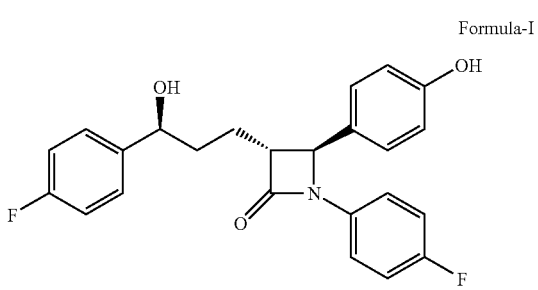

Formula-XI (h) Debenzylation of the compound of formula-XI with Pd/C to give the compound of formula-I.

Formula-I

DETAILED DESCRIPTION OF THE INVENTION

The present invention relates an improved process for the preparation of (3R,4S)-1-(4-Fluorophenyl)-3-[3(S)-3-(4-fluorophenyl)-3-hydroxypropyl)]-4-(4-hydroxyphenyl)-2-azetidinone, referred to here as (Ezetimibe).

The process of the present invention is schematically represented as follows.

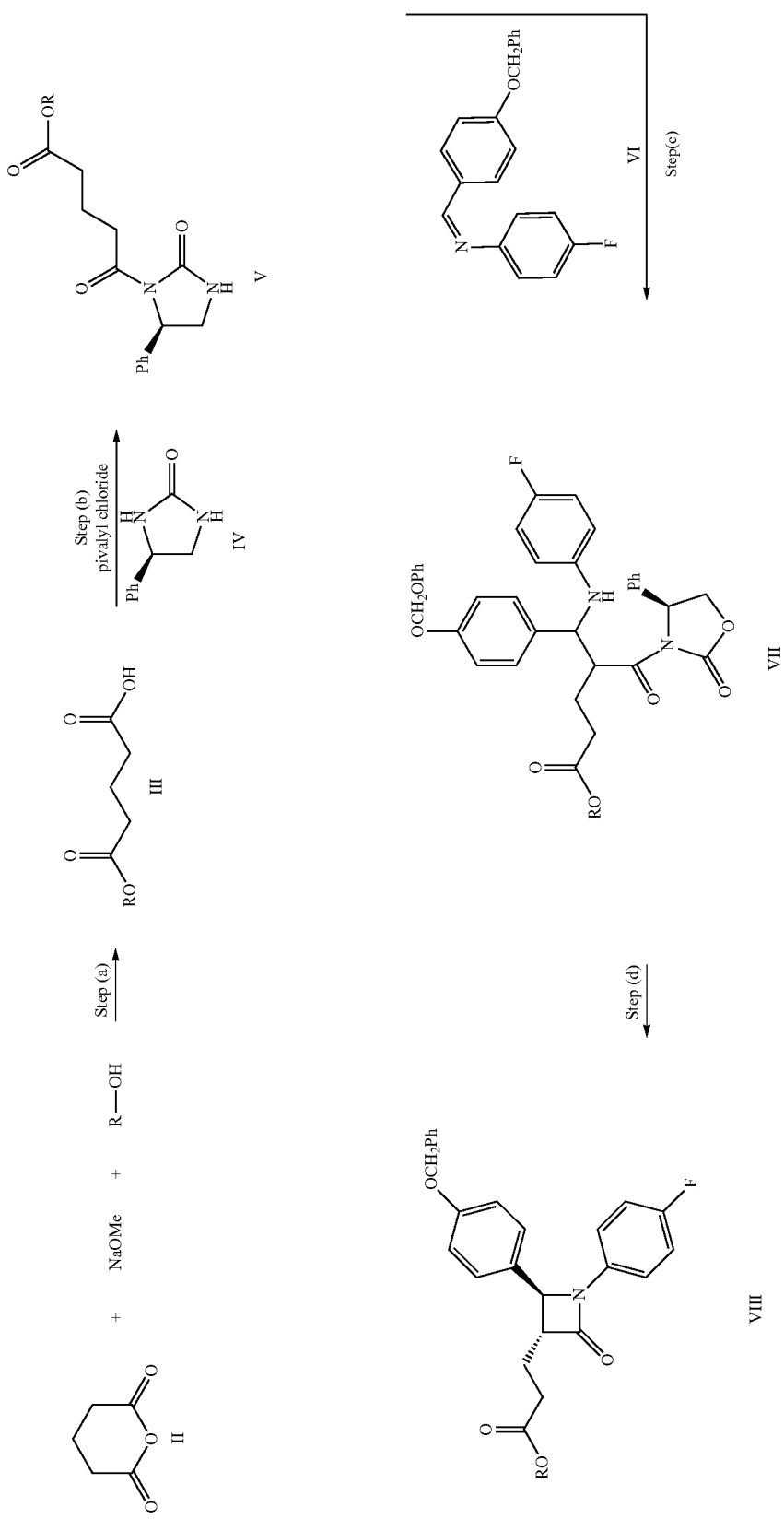

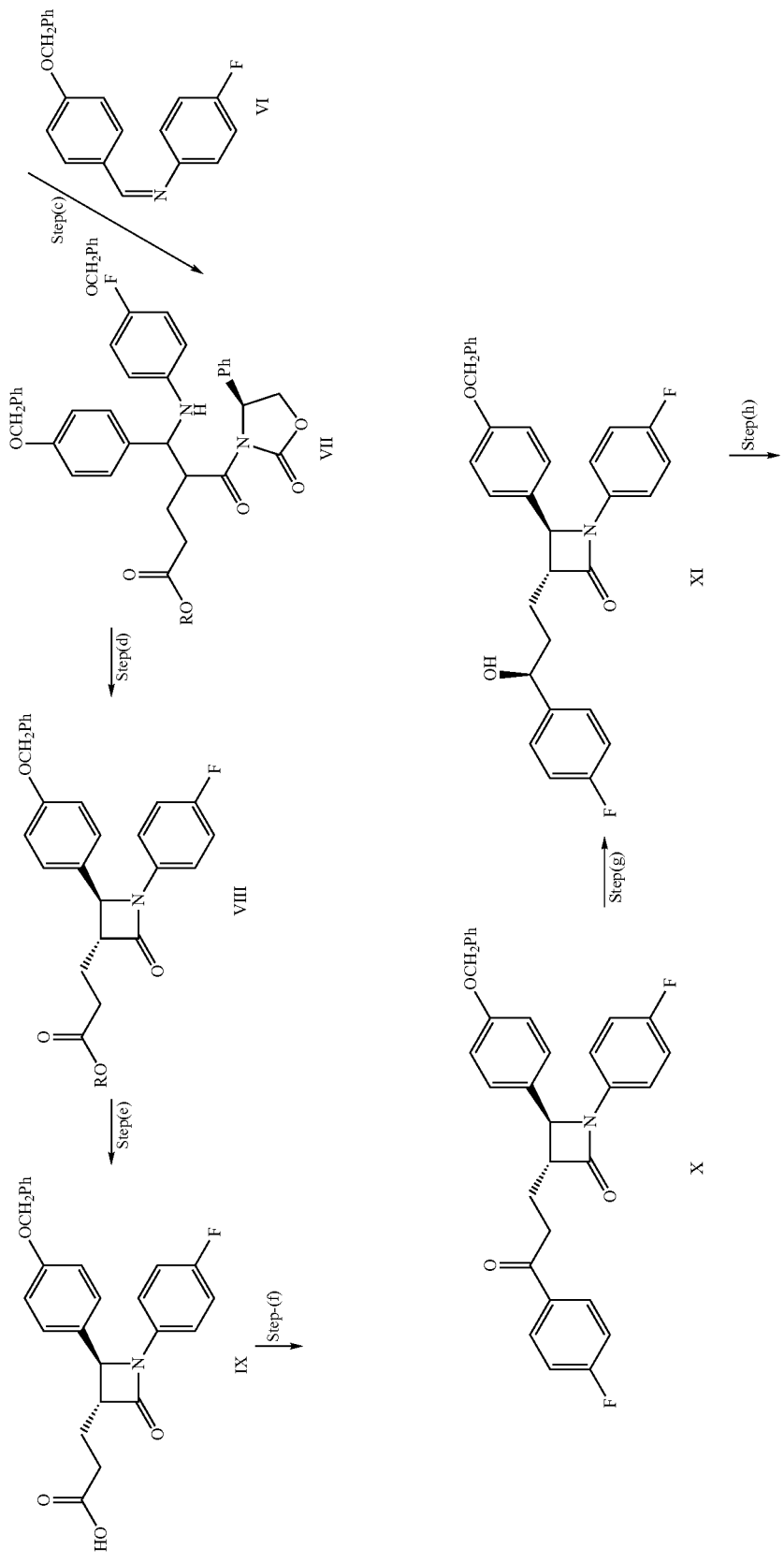

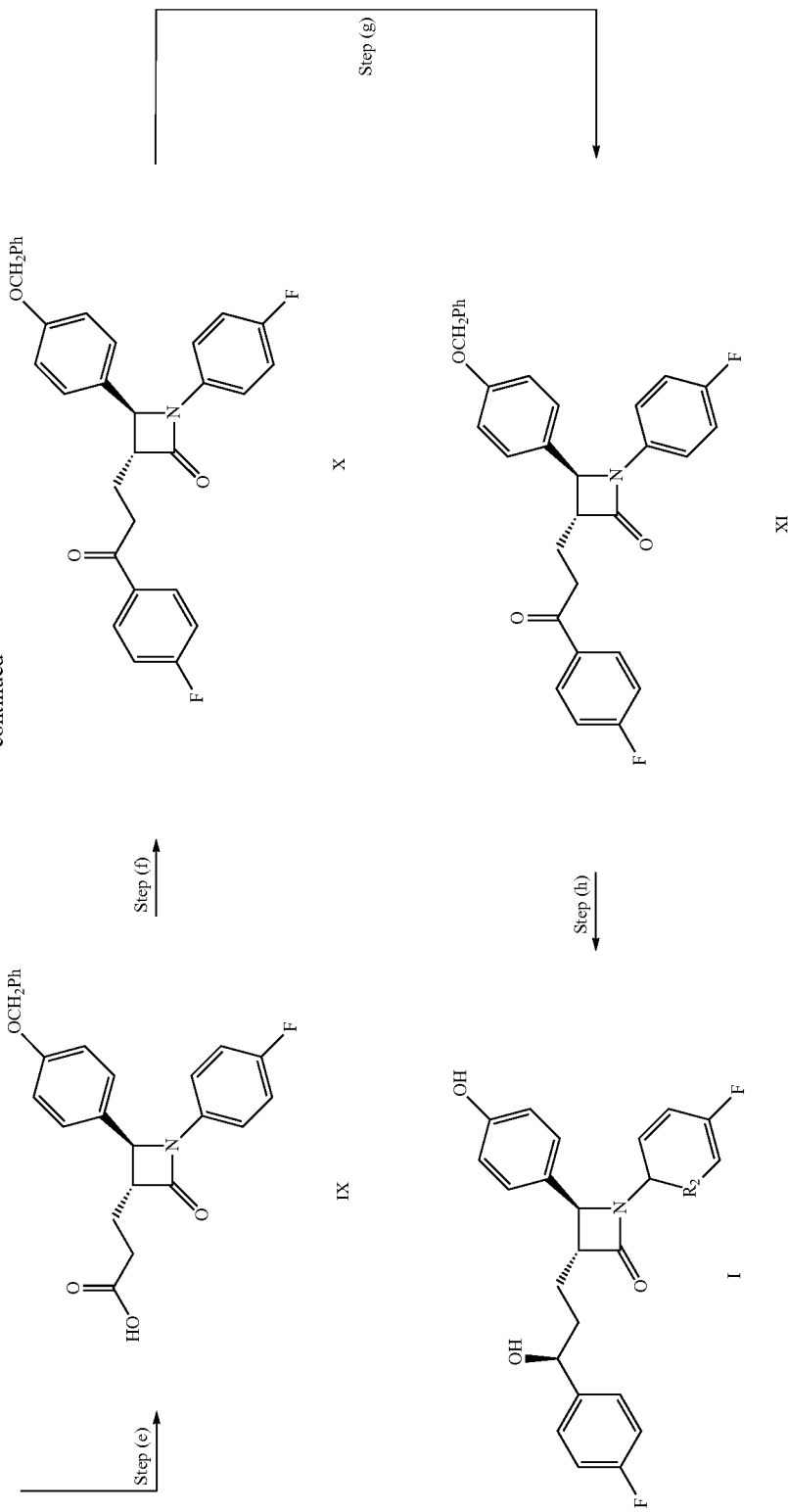

Comprising:
a. Reacting Glutaric anhydride of structural formula-II with an aliphatic alcohol or alicyclic alcohol in presence of a base sodium methoxide to give compound of formula-III.
b. Reacting the formula-III with pivalyl chloride in presence of a acid trapping agent like triethyl amine, diisopropyl ethyl amine or inorganic bases like sodium carbonate, potassium carbonate and further it is reacting with a chiral auxiliary of formula-IV to give ketone compound of structural formula of V.
c. Ketone compound of formula-V is further condensed with an benzylated imine of formula-VI to give the an amide compound of formula-VII in presence of a Lewis acid.
d. Cyclising the amide of formula-VII with a silylating agent and a fluoride ion catalyst as a cyclising agent to give the protected lactam compound of formula-VIII.
e. Hydrolysis of protected lactam compound of formula-VIII with a base to give the carboxylic acid of formula-IX.
f. Carboxylic acid of formula-IX is converts into acid chloride with oxalyl chloride and it is further condensed with para bromo fluoro benzene through organo metallic reaction to give the aromatic ketone of formula-X.
g. Reducing the ketone of formula-X with chiral reducing agent or in the presence of a chiral catalyst to give chiral alcohol of formula-XI.
h. Debenzylation of formula-XI with Pd/C to give the compound of formula-I.

Step-a: The reaction is carried out at a temperature −20° C. to 65° C., preferably at 25-35° C. for 30 minutes to 15 hrs, preferably 6-8 hrs.

Step-b: The pivaloyl chloride reaction is carried out in a suitable solvent like dichloromethane, toluene, xylene, chloroform, ethyl acetate, or a mixture thereof, preferably in dichloromethane, in the presence of an acid trapping agent such as triethyl amine, diisopropyl amine or an inorganic base like $NaHCO_3$, $Na_2CO_3$, $K_2CO_3$, preferably triethyl amine. Reaction is conducted at a temperature of ~10° C. to 50° C. preferably at 15-30° C. for 1 to 10 hours, preferably for 2-4 hours.

Chiral auxiliary such as the compound of formula-IV is used like S—POZ, S—BOZ, preferably S—POZ. This reaction is carried out inpresence of dimethyl amino pyridine as a catalyst at the temperature of 10-50° C., preferably at 40-50° C. for 30 minutes to 10 hrs, preferably 4-6 hrs.

Step-c: Condensation reaction of step-c can be carried out in a suitable solvent like dichloromethane, toluene, xylene, preferably dichloromethane and treated with a Lewis acid such as $TiCl_4$ at about −60 to 0° C., preferably at about −25° C., under a dry, inert atmosphere like nitrogen or orgon. A tert. amine base such as diisopropyl ethyl amine is used as a trapping agent. This reaction is conducted for 3-6 hrs at −25 to −10° C., preferably about 4 hrs or until reaction is completely by TLC.

Step-d: The cyclisation of step-d can be carried out in a suitable solvent like dichloro methane, toluene, xylene, ethyl acetate, preferably in toluene at a temperature 0° C. to 80° C., preferably at 40-50° C. with silylating agent like bis trimethyl silyl acetamide and a cyclising agent like tetra butyl ammonium fluoride.

Step-e: Hydrolysis of formula VIII is carried out in a suitable solvent like an alcohol solvent, like ethanol, isopropyl alcohol or tert-butanol, or a ketonic solvent, like acetone or methyl isobutyl ketone, or a mixture thereof, preferably in acetone, with a base like alkali and alkaline earth metal hydroxides, alkali or alkaline earth metal alkoxides, carbonates or bicarbonates, preferably sodium hydroxide, at a temperature of 0° C. to 50° C., preferably at 25-35° C., for 30 minutes to 10 hours, preferably 2-3 hours, to obtain a carboxylic acid of formula IX. Adjusting the pH of the reaction mass to 5-7, preferably 6.5 to 7.0 and extraction of carboxylic acid compound.

Step-f: Converting the Carboxylic acid of formula-IX into acid chloride using acid halogenating agent like, oxalyl chloride, thionyl chloride and phosphorous halides, preferably with oxalyl chloride and with a suitable solvent like dichloromethane, toluene, xylene or ethyl acetate, preferably dichloroinethane. This reaction is carried out an inert atmosphere like nitrogen at 0-40° C. for 10 minutes 5 hrs. Preferably at 25-35° C. for 1-3 hrs Acid chloride is further condensed with a Grignard reagent (it is prepared from the reaction of para bromo fluoro benzene with magnesium turnings to form 4-fluoro phenyl magnesium bromide and it is further converted to 4-fluoro phenyl zinc halide with anhydrous zinc chloride) in the presence of a transition metal catalyst like palladium, cobalt, nickel, iron, or rhodium having its anionic part either halides or acetates to give the condensed product as formula X. The palladium catalyst is palladium acetate or palladium chloride, preferably palladium acetate. This reaction is carried out with a suitable solvent like dichloromethane, toluene, xylene or ethyl acetate, preferably toluene. This reaction is carried out in an inert atmosphere like nitrogen at −10° C. to 40 ° C. for 10 minutes to 3.00 hours. Preferably at 10-15° C. for 30-60 minutes.

Step-g: Reduction of ketone of formula-X to hydroxy group using a chiral reducing agent such as DIP Chloride or reducing agent Borane THF or Borane-DMS, in the presence of a chiral catalyst such as (R)-tetrahydro-1-methyl-3,3-diphenyl-1H,3H-pyrrol(1,2-c)(1,3,2)oxaza-borolidine (R-Methyl CBS) or R-Butyl CBS or R-Phenyl CBS. This reaction is carried out at ambient temperature in a suitable solvent like dichloromethane, toluene, xylene or ethyl acetate, or a mixture thereof, preferably toluene. This reaction is carried out under an inert atmosphere like nitrogen at −10° C. to 40 ° C. for 30 minutes to 10 hours, and preferably at 0 to 5° C. for 2-3 hours.

Step-h: Debenzylation of formula-XI with palladium carbon to give the title compound of formula-I. This reaction is carried out at with a suitable solvent like an alcoholic solvents like methanol, IPA, tert-butanol or dichloromethane, toluene preferably in IPA. This reaction is carried out at 10 to 70° C. for 30 minutes 10 hrs. Preferably at 45 to 50° C. for 2-3 hrs.

The examples mentioned below demonstrate specific preparations of the present invention. The examples are provided to illustrate the details of the invention and should not be constrained to limit the scope of the present invention.

EXAMPLE: 1

Preparation of (3R,4S)-1-(4-Fluorophenyl)-3-[3(S)-3-(4-fluorophenyl)-3-hydroxypropyl)]-4-(4-hydroxyphenyl)-2-azetidinone, referred to here as Formula-1

Step-a: Preparation of Monomethyl glutarate (Formula-III)

Taken 100 gm of glutaric anhydride of formula-II and methanol (250 ml) and sodium methoxide (1 gm) in a 1 lit round bottom flask and stirred for 6 hrs at 25-35° C. Distilled the solvent completely under vacuum at below 60° C. Residue is taken to next stage directly without any purification. Yield: 125 gm

Step-b: Preparation of Ketone Compound of Formula-V

Formula-III material (45 gm) is dissolved in dichloromethane (225 ml) in 1 lit cleaned RBF. Added triethyl amine to the reaction mixture and stirred for 10 minutes. Pivaloyl chloride is added to the reaction mass in 45 minutes at 25-35° C. Maintained the reaction mass for 2 hrs. Added S—POZ (formula-IV), DMAP and DMF to the refluxed the reaction mixture for 7 hrs. Reaction mixture is quenched with water and separated the organic layer. Organic layer washed with water (100 ml) and distilled the solvent completely under vacuum and recrystallised the material in pet-ether. Yield: 50 gm.

Step-c: Preparation of Compound of Formula-VII

Titanium tetrachloride (18 ml) and dichloromethane (600 ml) were taken into a clean RBF, cooled the reaction mixture to 0° C. and added titanium isopropoxide (16 ml) at 0-5° C. Dissolved the Formula-V material (50 gm) in dichloromethane and added to the reaction mass at 0-5° C. and maintained the reaction mass for 15 minutes. Diisopropyl ethyl amine (65 ml) is added to the reaction mixture and maintained for 45 minutes and cooled to −20 to −10° C. and charged the benzylated imine (92 gm) of formula-VI to the reaction mixture, maintained for 4 hrs at −20 to −10° C. Quenched the reaction with acetic acid and washed the organic layer with sulfuric acid solution, distilled the solvent completely and material is recrystalised in methanol. Yield: 65 gm.

Step-d: Preparation of Compound of Formula-VIII (Cyclisation)

Taken toluene (100 ml) and compound of formula VII (25 gm) into cleaned RB.Flask, heated to 45° C. and added N,O-bis trimethyl silyl acetamide (17 gm) and TBAF.3H$_2$O (1.1 gm) and maintained for 2 hrs at 45-50° C. Reaction mass is quenched with methanol and washed with 1 N Hcl solution, 1N sodium bicarbonate solution followed by saturated sodium chloride solution, distilled the solvent completely under vacuum and toluene is charged and isolated Rec S—POZ, filtrate is concentrated and product is isolated in methanol and dried the product at 50-60° C. (Yield: 13 gm). M.R 60-65° C.

Step-e: Preparation of Compound of Formula-IX

Compound of formula-VIII (25 gm) is dissolved in acetone (25 ml) in a cleaned R.B.Flask. Water (62.5 ml) and sodium hydroxide (2.8 gm) added to the reaction mass. Maintained the reaction mass for 3 hrs at ambient temperature. Reaction mass quenched with water and pH adjusted to 6.5-7.0 with aqueous hydrochloric acid. Reaction mass extracted with ethyl acetate and distilled the solvent completely under vacuum to give residue of the compound. It is used into next stage without any purification.
Yield: 22 gm.

Step-f: Preparation of Compound of Formula-X

Compound of formula-IX (25 gm) is dissolved in dichloromethane in a R.B.Flask. and catalytical amount of Dimethyl formamide is added. Oxalyl chloride is slowly added at ambient temperature, maintained the reaction mass for 3 hrs at ambient temperature. Distilled the solvent completely under vacuum and toluene is added and again distilled completely under vacuum. Toluene is added to the crude and cooled to 10-15° C. and then the palladium acetate and maintained for 15 minutes.

4-fluorophenyl magnesium bromide is taken in another vessel under nitrogen atmosphere and cooled to 0-5° C. and added anhydrous zinc chloride and stirred for 1 hr. This complex is added to the acid chloride reaction mass at ambient temperature and maintained for 45 minutes. Filtered the reaction mass through hyflow and washed with toluene and THF mixed solution. Distilled the solvent completely under vacuum, added dichloromethane and silica gel to the crude and distilled the solvent completely under vacuum, Cyclohexane is added to the silicagel mixture and stirred for 30 minutes and filtered and washed with cyclohexane. Silicagel mixture is slurried with ethyl acetate and cyclohexane. Distilled both filtrates under vacuum to get the residue. (Yield: 18 gm).

Step-g

EXAMPLE-1

Preparation of Compound of Hydroxy Compound of Formula-XI

Taken toluene (250 ml) into cleaned R.B.Flask under nitrogen atmosphere and cooled to 0-5° C. Borane DMS complex and (R)-tetrahydro-1-phenyl-3,3-diphenyl-1H,3H-pyrrol (1,2-c)(1,3,2)oxaza borolidine (R-phenyl CBS) is charged into the reaction mass at 0° C. 25 gm of Keto compound of formula-X is dissolved in toluene (50 ml) and added to the reaction mass at 0-5° C. Maintained the reaction mass for 3 hrs and quenched with methanol and followed by 1 N hydrochloric acid solution. Organic layer separated and washed with 5% hydrogen peroxide solution and 5% sodium sulfate solution and followed by with 10% sodium chloride solution. Distilled the solvent completely under reduced pressure at below 75° C. Product is isolated in diisopropyl ether and dried the product at 60-70° C. for 6 hrs. (Yield: 15 gm).

EXAMPLE-2

Preparation of compound of hydroxy compound of formula-XI

Taken toluene (250 ml) into cleaned R.B.Flask under nitrogen atmosphere and cooled to 0-5° C. DIP Chloride (Mole ratio 1:1.5) into the reaction mass at 0° C. 25 gm of keto compound of formula-X is dissolved in toluene (50 ml) and added to the reaction mass at 0-5° C. Maintained the reaction mass for 3 hrs and quenched with ammonia solution. Organic layer separated and washed with 10% sodium chloride solution. Distilled the solvent completely under reduced pressure at below 75° C. Residue is taken for next stage directly without any purification.

Step-h: Preparation of compound of Formula-I (Ezetimibe)

Taken compound of formula-XII (10 gm) and isopropanol (100 ml) into a hydrogenation flask, added 5% Pd/C (4 gm) at 25° C. and maintained at 45-50° C. for 3 hrs under hydrogen pressure, filtered through hyflow and washed the Pd/C with isopropanol (20 ml). Distilled the solvent completely under vacuum at below 70° C., product is recrystallised in dichloromethane (Yield: 6 gm).

Purification of Ezetimibe (Formula-1).

Ezetimibe (10 gm) is dissolved in 30 ml of methanol and filtered through hyflow and saturated with DM. Water (30 ml) and stirred for 1 hr at 20-25° C. Product filtered and dried for 6-8 hrs at 80-85° C. (Yield: 9 gm).

We claim:

1. A process for the preparation of (3R,4S)-1-(4-Fluorophenyl)-3-[(3S)-3-(4-fluorophenyl)-3-hydroxypropyl]-4-(4-hydroxyphenyl)-2-azetidinone (Ezetimibe) compound of formula (I)

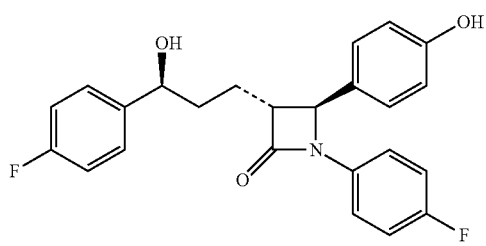

comprising:

(a) reacting glutaric anhydride compound of formula (II) with linear or branched chain aliphatic C1-C6 alcohols in presence of a base to give alkyl ester compound of formula (III)

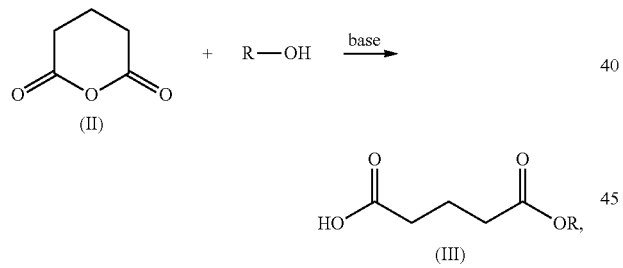

wherein R is C1-C6 alkyl;

(b) reacting the compound of formula (III) with pivaloyl chloride in presence of an acid trapping agent, and subsequently reacting the product with a chiral auxiliary compound of formula (IV) to give ester compound of formula (V)

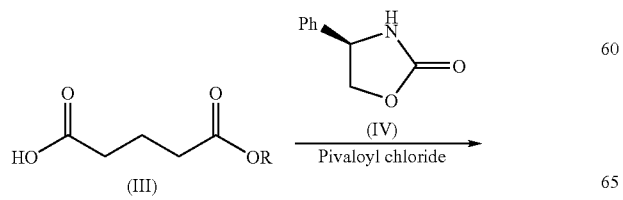

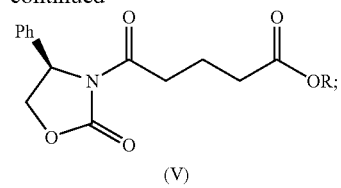

(c) reacting the ester compound of formula (V) with benzylated imine compound of formula (VI) in presence of a Lewis acid to obtain an amide compound of formula (VII)

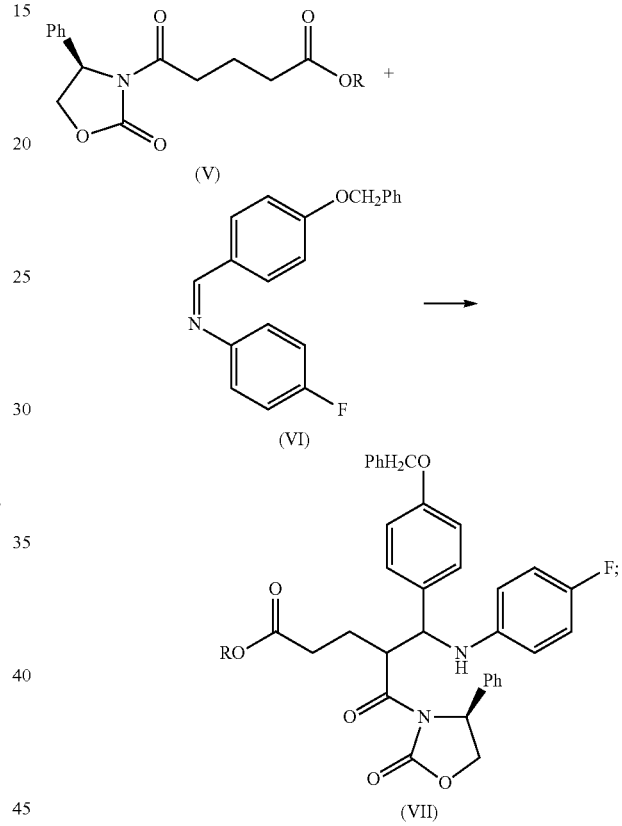

(d) cyclizing the amide compound of formula (VII) with (i) a silylating agent and (ii) a fluoride ion catalyst cyclizing agent in a solvent to obtain the compound of formula (VIII)

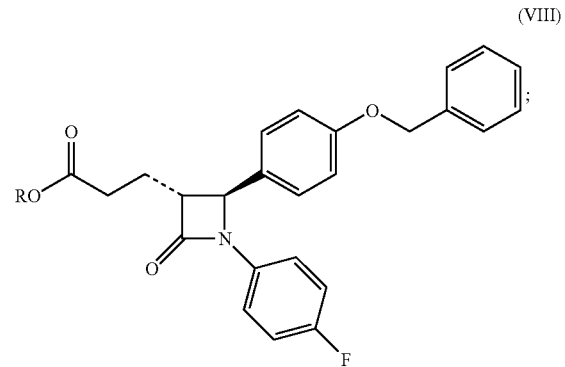

(e) hydrolyzing the ester group of compound of formula (VIII) with a base in a solvent, followed by adjusting the pH of the reaction mixture to 5-7, and followed by extracting the carboxylic acid compound of formula (IX)

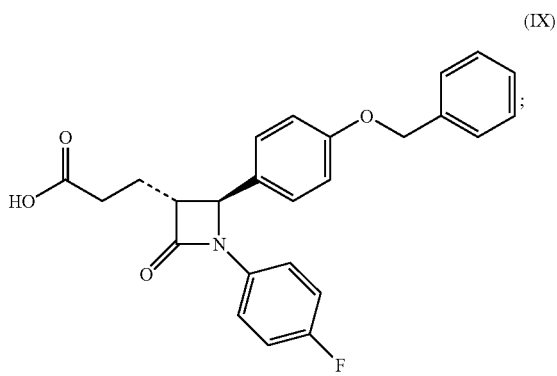

(f) reacting the compound of formula (IX) with oxalyl chloride in a first solvent to form an acid chloride product, followed by reacting the product acid chloride compound in situ with 4-fluorophenyl zinc halide in the presence of palladium(II) acetate in a second solvent, thereby producing the aromatic ketone compound of formula (X)

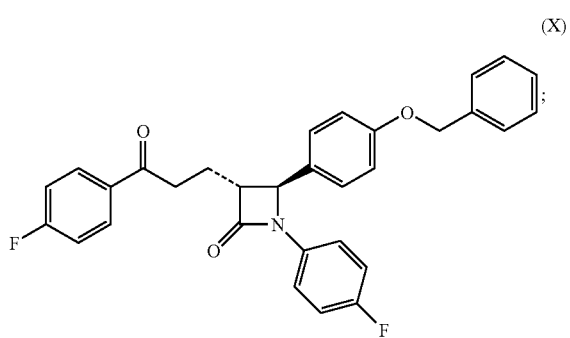

(g) reducing the aromatic ketone compound of formula (X) in presence of a chiral reducing agent alone or in combination with a chiral catalyst in a solvent to obtain hydroxy compound of formula (XI), followed by isolating the hydroxy compound of formula (XI) as a solid using an organic solvent,

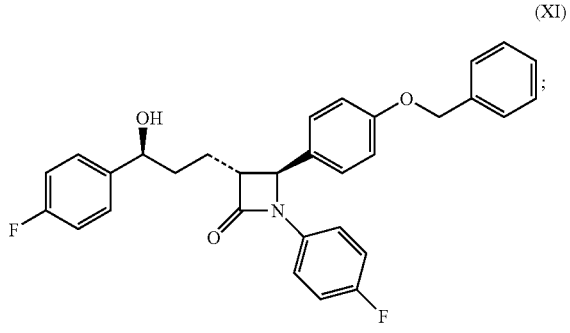

(h) debenzylating the compound of formula (XI) with palladium carbon in an alcoholic solvent or dichloromethane or toluene to produce the compound of formula (I)

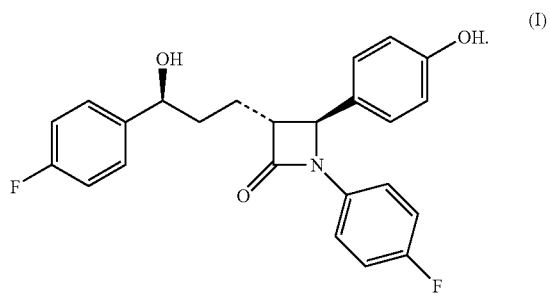

2. The process of claim 1, wherein the C1-C6 alcohol used in step (a) is methanol.

3. The process of claim 1, wherein the base used in step (a) is sodium methoxide.

4. The process of claim 1, wherein the acid trapping agent of step (b) is triethyl amine, diisopropyl ethyl amine, sodium carbonate, or potassium carbonate.

5. The process of claim 1, wherein the chiral auxiliary compound in step (b) is (S)-4-phenyl-2-oxazolidinone (S—POZ) or (S)-4-benzyl-2-oxazolidinone.

6. The process of claim 1, wherein the Lewis acid used in step (c) is titanium tetrachloride.

7. The process of claim 6, wherein the Lewis acid used in step (c) is titanium tetrachloride in combination with titanium isopropoxide.

8. The process of claim 1 wherein the silyating agent used in step (d) is N,O-bis trimethyl silyl acetamide.

9. The process of claim 1, wherein the fluoride ion catalyst cyclizing agent used in step (d) is tetra butyl ammonium fluoride.

10. The process of claim 1, wherein the solvent used in step (d) is methylene chloride, toluene, xylene, or ethyl acetate.

11. The process of claim 1, wherein the base used in step (e) is an alkali or alkaline earth metal alkoxide, an alkali or alkaline earth metal hydroxide, a carbonate or a bicarbonate.

12. The process of claim 11, wherein the base used in step (e) is an alkali earth metal hydroxide.

13. The process of claim 12, wherein the base used in step (e) is sodium hydroxide.

14. The process of claim 1, wherein the solvent used in step (e) is an alcohol solvent or a ketonic solvent.

15. The process of claim 14, wherein the alcohol solvent used in step (e) is ethanol, isopropyl alcohol, or tertiary butanol and the ketonic solvent is acetone, or methyl isobutyl ketone.

16. The process of claim 1, wherein the pH of the reaction mixture is adjusted to between 6.5 and 7.0 in step (e).

17. The process of claim 1, wherein the chiral reducing agent used in step (g) is β-chlorodiisopinocampheylborane (DIP chloride).

18. The process of claim 1, wherein the reducing agent used in step (g) is borane THF or borane DMS in combination with the chiral catalyst.

19. The process of claim 1, wherein the chiral catalyst used in step (g) is (R)-tetrahydro-1-methyl-3,3-diphenyl-1H,3H-pyrrolo(1,2-c)(1,3,2) oxazaborole (R-Methyl CBS), R-Butyl CBS, or R-Phenyl CBS.

20. The process of claim 1, wherein the reaction in step (g) is carried out at ambient temperature.

21. The process of claim 1, wherein the solvent used in step (g) is methylene chloride, toluene, xylene, ethyl acetate or a mixture thereof.

22. The process of claim 1, wherein the organic solvent used in step (g) is toluene or diisopropyl ether.

23. The process of claim 22, wherein the organic solvent used in step (g) is diisopropyl ether.

24. A process for the preparation of the compound of formula (X) from the compound of formula (IX), comprising:

reacting the compound of formula (IX)

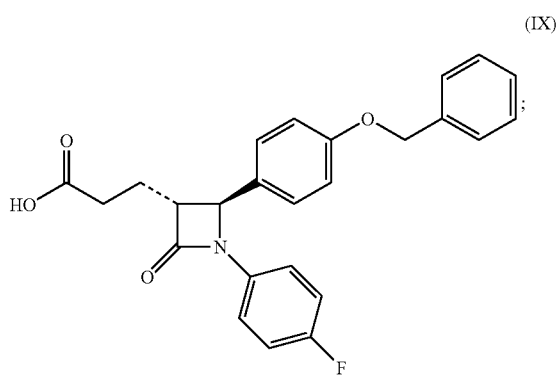

(IX)

with oxalyl chloride in a first solvent, followed by reacting the product acid chloride compound in situ with 4-fluorophenyl zinc halide in the presence of palladium(II) acetate in a second solvent, thereby producing the aromatic ketone compound of formula (X)

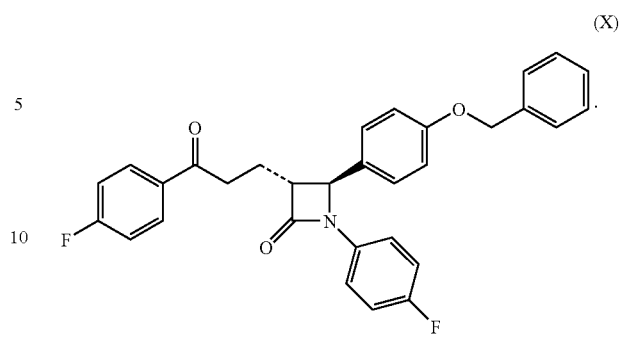

(X)

25. The process of claim 24, further including the steps of:
    isolating the compound of formula (X);
    adding silica gel and dichloromethane to the compound of formula (X);
    removing the dichloromethane;
    adding cyclohexane or a mixture of cyclohexane and ethyl acetate to the compound of formula (X) and silica gel, thereby forming a slurry; and
    filtering the slurry, thereby separating the silica gel from the compound of formula (X).

26. The process of claim 19, wherein step (g) further includes washing a mixture of the hydroxy compound of formula (XI) in the solvent with 5% hydrogen peroxide solution and 5% sodium sulfate solution, followed by 10% sodium chloride solution before isolating the hydroxy compound of formula (XI) as a solid.

27. The process of claim 1, wherein step (f) further includes the steps of:
    isolating the compound of formula (X);
    adding silica gel and dichloromethane to the compound of formula (X);
    removing the dichloromethane;
    adding cyclohexane or a mixture of cyclohexane and ethyl acetate to the compound of formula (X) and silica gel, thereby forming a slurry; and
    filtering the slurry, thereby separating the silica gel from the compound of formula (X).

* * * * *